United States Patent [19]
Timm et al.

[11] 3,987,789
[45] Oct. 26, 1976

[54] MALLEABLE PENILE PROSTHESIS

[75] Inventors: Gerald W. Timm; John H. Burton, both of Minneapolis, Minn.

[73] Assignee: American Medical Systems, Inc., St. Louis Park, Minn.

[22] Filed: Oct. 28, 1975

[21] Appl. No.: 626,373

[52] U.S. Cl. ..................................... 128/79; 3/1
[51] Int. Cl.² ....................... A61F 5/00; A61F 5/42
[58] Field of Search .......... 128/79, 92 BC, 68, 68.1; 3/1

[56] References Cited
UNITED STATES PATENTS

| | | | |
|---|---|---|---|
| 3,832,996 | 9/1974 | Kalnberz | 128/79 |
| 3,893,456 | 7/1975 | Small et al. | 128/79 |

OTHER PUBLICATIONS
Pearman–Dow Corning Bulletin, July 1966, p. 10.

*Primary Examiner*—Lawrence W. Trapp
*Attorney, Agent, or Firm*—Williamson, Bains & Moore

[57] ABSTRACT

A prosthesis adapted to be implanted in the penis for simulating an erection is disclosed herein. The prosthesis includes an elongated, malleable rod portion which is housed within a generally tubular, physiologically inert plastic body. The malleable rod portion enables the prosthesis to be conformed to a variety of shapes by bending or twisting same. During intercourse the prosthesis will maintain the penis in an erectile state, and afterwards the penis may be positioned and maintained by the prosthesis in a convenient, comfortable position.

7 Claims, 7 Drawing Figures

MALLEABLE PENILE PROSTHESIS

BACKGROUND OF THE INVENTION

This invention relates to the treatment of erectile impotence. More particularly, the present invention relates to an artificial prosthesis which may be implanted in a flaccid penis for enabling the achievement of an erectile state.

The causes of male impotence are many and varied. Impotence can be caused, for example, by neurological diseases or injury.

Several systems for treating impotence are known in the prior art. Elongated, splint-type devices for external attachment to the penis are shown in U.S. Pat. No. 1,462,000, issued on July 17, 1923 to A. Bennett and U.S. Pat. No. 3,446,206, issued on May 27, 1926 to A. De Lano. The latter two devices are externally attached to the penis by a means of an elastic band or cord. U.S. Pat. No. 3,773,040, issued on Nov. 20, 1973 to G. Gavrilovich discloses an elongate flexible band which may be externally wound around the penis to restrict the back flow of venus blood therein in order to approximate an erection.

Another prior art approach to remedying impotence has been to develop a penile prosthesis which may be implanted within the penis to simulate the erectile state. An example of an implantable penile prosthesis is shown in U.S. Pat. No. 3,893,456 issued on July 8, 1975. The latter reference discloses a prosthesis comprising an elongated, stiff rod which is encapsulated within an elongated, soft plastic housing. A pair of such rods are adapted to be surgically implanted within the corpora cavernosa regions of the penis to maintain a constant erectile state. Another implantable prosthesis is shown in U.S. Pat. No. 3,853,122, issued to Strauch et al on Dec. 10, 1974. The latter device includes an elongated, expansible, flexible tube which is adapted to be implanted in the penis longitudinally therewithin. A flexible pump is provided to inflate the prosthesis to produce a simulated erection when desired.

The inconvenience and general undesirability of external apparatus for producing an erectile state is obvious and apparent. The implantation of stiff rods within the penis provides a desired erectile state but can be physically uncomfortable and emotionally disconcerting. Another disadvantage associated with a rigid, stiffly flexible penile prosthesis such as that disclosed in U.S. Pat. No. 3,893,456 is that special undergarments may be required to restrain the penis in a position of concealment.

SUMMARY OF THE INVENTION

The instant invention comprises a malleable prosthesis adapted to be surgically implanted within the penis. The prosthesis may be conformed to any desired shape so that intercourse is facilitated, and, afterwards, the penis may be comfortably bent to a concealment position.

The prosthesis comprises an internally disposed, elongated malleable rod portion preferably comprised of a nickel-titanium alloy sold under the trade name "Nitinol." A generally tubular, physiologically inert housing surrounds the rod and provides an encapsulating covering. In the preferred embodiment the covering additionally comprises a solid rear tip portion which anchors the prosthesis in the desired internal position. The covering or housing is preferably comprised of silastic.

Thus, an object of the present invention is to provide a controllable penile erection prosthesis for treating erectile impotence.

Another object of this invention is to minimize physical discomfort associated with prior art implants of the type described. An important feature of this invention is that the prosthesis may be bent or twisted by the patient in order to manipulate the penis into a comfortable or desirable position.

Another object of this invention is to provide a penile prosthesis of the character described which may be implanted internally of the patient's body and which will not require external apparatus.

Still another object of this invention is to provide apparatus of the character described which will be physiologically compatible with the patient's internal organs.

Yet another object of the invention is to provide a penile prosthesis which can be easily and quickly implanted through conventional medical/surgical techniques. It is a feature of this invention that the apparatus is adapted to be installed internally of the penis within the corpora cavernosa regions therein.

These and other objects of this invention, along with features of novelty appurtenant thereto, will appear or become apparent in the course of the following description.

BRIEF DESCRIPTION OF THE DRAWINGS

In the following drawings which form a part of the specification and are to be construed in conjunction therewith, and in which like reference numerals have been employed to indicate like parts in the various views.

DETAILED DESCRIPTION OF THE DRAWINGS

Figure 1:
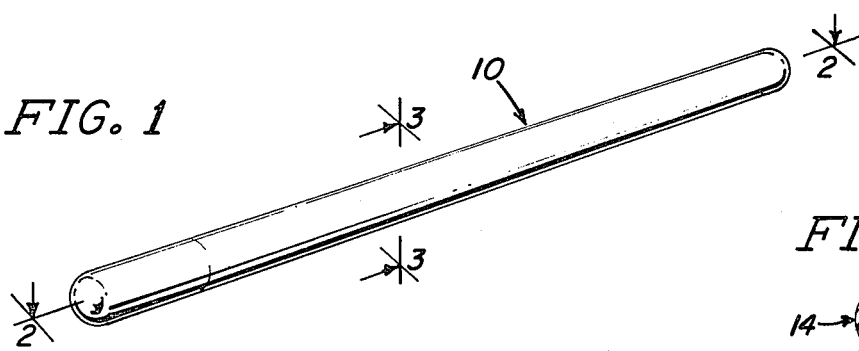
FIG. 1 is a perspective view of a malleable penile prosthesis constructed in accordance with the teachings of this invention.
Figure 3:
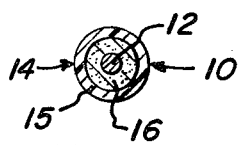
FIG. 3 is a sectional view taken along line 3—3 in FIG. 1.
Figure 2:
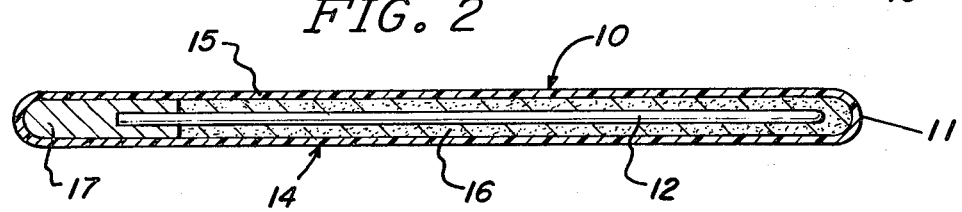
FIG. 2 is a longitudinal sectional view of the prosthesis taken along line 2—2 of FIG. 1.

As seen in FIGS. 1 through 3, the prosthesis 10 is of generally elongated construction. The prosthesis includes an internally-disposed malleable rod portion 12 and a flexible outer body portion 14 which surrounds rod 12 and isolates same from the internal body organs. The elongated rod 12 is preferably comprised of a nickel titanium alloy sold under the trade name Nitinol, and available from Titanium Metals Inc. in Toronto, Ohio. Alternatively rod 12 may be comprised of other malleable substances or metals such as copper or the like. While in the preferred embodiment rod 12 is of generally solid construction, it may be comprised of a plurality of stranded filaments or wires.

Body portion 14 which is preferably comprised of physiologically inert silastic, preferably includes an outer silastic skin portion 15, an inner flexible foam portion 16 disposed between outer skin 15 and the internal rod 12, and a generally solid end portion 17. Portion 17 functions to anchor the prosthesis in the desired position within the penis.

Figure 4:
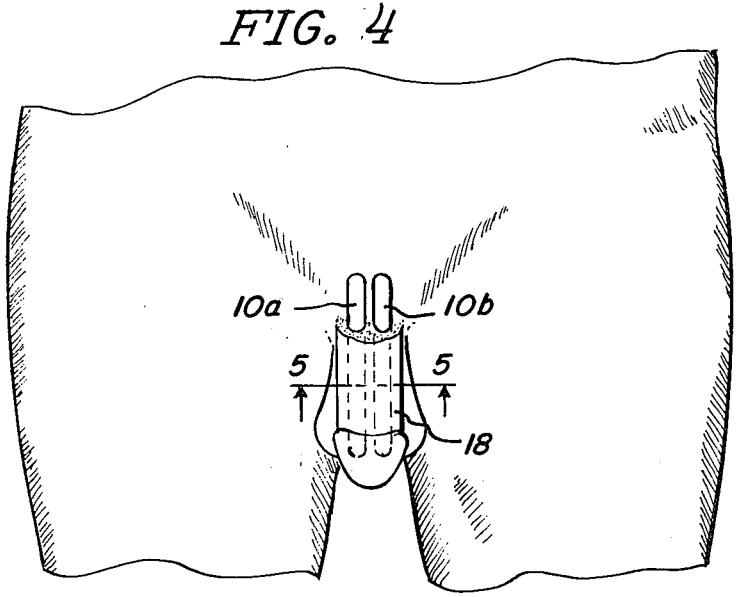
FIG. 4 is a front sectional view of the trunk of a male patient in which the prosthesis has been implanted.
Figure 5:
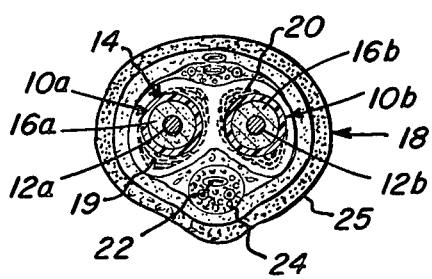
FIG. 5 is a pictorial cross sectional view of a penis in which a prosthesis has been implanted in each of the corpora cavernosa regions therein.

While a penile erection may be achieved through the use of one prosthesis, a pair may be used as illustrated in FIG. 4. Prosthesis 10a and 10b have been surgically implanted within the corpora cavernosa regions of the penis longitudinally parallel to the axis of the penis 18. The placement of the apparatus is disclosed in cross section of FIG. 5. The parallel corpora cavernosa regions 19 and 20 extend longitudinally through the penis interior. For clarity, the urethra 22, the corpus spongiosum 24, and the outer skin 25 have been identified.

Figure 7:
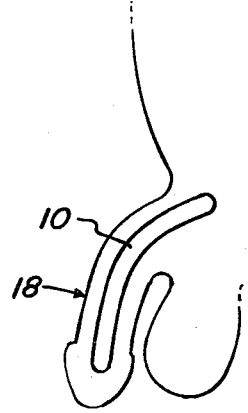
FIG. 7 is a pictorial view showing the penis with the prosthesis inserted, the penis being positioned in a comfortable, out-of-the-way position.
Figure 6:
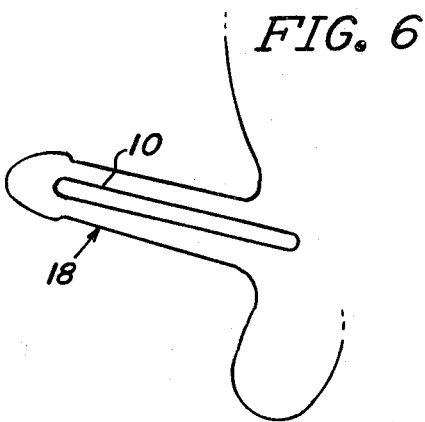
FIG. 6 is a pictorial view showing the penis in a simulated erectile state.

After the apparatus 10 has been properly installed interiorly of the penis, the penis may be oriented as in FIG. 6 when sexual intercourse is desired. The rigidity of the rod portion 12 will enable the penis to function during sexual intercourse. Afterwards, because of the malleability of the rod portion 12, the penis 18 may be bent downwardly as shown in FIG. 7. Alternatively, the penis may be manipulated into any other convenient or comfortable position by the patient. The malleable inner rod element 12, when bent, will retain the shape to which it is formed, and will hold the penis in any desired set position. Because of the construction disclosed, the use of special undergarments is obviated and the emotional and/or physiological discomfort associated therewith is minimized.

The apparatus is implanted within the penis through conventional surgical techniques. One such technique is disclosed in a co-pending patent application owned by the same assignee as in the instant case, filed on July 19, 1974 and bearing Ser. No. 490,083. The latter application is hereby incorporated by reference.

Briefly summarized, the surgical insertion procedure involves the making of an abdominal incision through the patient's skin to provide access to the pelvic cavity. Erectile tissues within the copora cavernosa regions of the penis are displaced by an inserted rod in order to create space for subsequent insertion of the prosthetic devices 10. The shape of the prosthesis enables quick insertion into the corpora regions. The end 11 of the prosthesis is first inserted into the corpora regions, until prosthesis anchored portion 17 is positioned within the pubic synthesis of the patient. Obviously a variety of diameters and lengths of the prosthesis can be employed where necessary to accommodate differing physical needs.

While a preferred embodiment of the present invention has been described, it should be understood that various changes, adaptations and modifications may be made therein without departing from the spirit of the invention and the scope of the appended claims.

What is claimd is:

1. A prosthesis adapted to be implanted in a penis for treating erectile impotence, said prosthesis comprising:
    at least one elongated, malleable rod portion adapted to be selectively conformed to a desired shape; and
    a generally tubular, physiologically inert covering for encapsulating said rod portion(s).

2. The prosthesis as in claim 1 wherein said covering comprises a solid rear tip portion for anchoring said prosthesis within the penis.

3. The prosthesis as in claim 1 wherein said covering is comprised of silastic.

4. The prosthesis as in claim 1 wherein said outer covering includes an inner foam layer and an outer skin layer.

5. The prosthesis as in claim 1 wherein the diameter of said prosthesis is substantially equal to the diameter of the corpora cavernosa regions within the penis.

6. The prosthesis as in claim 5 wherein said rod is comprised of a nickel titanium alloy.

7. The prosthesis as in claim 5 wherein said rod is comprised of a plurality of stranded filaments.

* * * * *